United States Patent
Yusuf et al.

(10) Patent No.: US 9,579,434 B2
(45) Date of Patent: Feb. 28, 2017

(54) FLEXIBLE MAGNETIC MEMBRANE BASED ACTUATION SYSTEM AND DEVICES INVOLVING THE SAME

(75) Inventors: Seikh Mohammad Yusuf, India (IN); Komarakshi Rajagopalan Balakrishnan, Adyar Chennai (IN); Jatinder Vir Yakhmi, Mumbai (IN)

(73) Assignee: THE SECRETARY OF ATOMIC ENERGY, GOVT. OF INDIA, Mumbai, Maharashtra (IN)

( * ) Notice: Subject to any disclaimer, the term of this patent is extended or adjusted under 35 U.S.C. 154(b) by 0 days.

(21) Appl. No.: 13/582,084

(22) PCT Filed: Mar. 3, 2010

(86) PCT No.: PCT/IN2010/000123
§ 371 (c)(1),
(2), (4) Date: Aug. 31, 2012

(87) PCT Pub. No.: WO2011/107996
PCT Pub. Date: Sep. 9, 2011

(65) Prior Publication Data
US 2012/0323318 A1    Dec. 20, 2012

(51) Int. Cl.
*A61M 1/10* (2006.01)
*F04B 43/04* (2006.01)

(52) U.S. Cl.
CPC ........ *A61M 1/1053* (2013.01); *A61M 1/1055* (2014.02); *A61M 1/1068* (2013.01);
(Continued)

(58) Field of Classification Search
USPC ................................ 623/3.1, 3.11, 3.16–3.25
See application file for complete search history.

(56) References Cited

U.S. PATENT DOCUMENTS 3,733,616 A  *  5/1973  Willis, Jr. .................... 623/3.11
4,649,339 A     3/1987  Grangroth et al.
(Continued)

FOREIGN PATENT DOCUMENTS

DE    102007051977    *  9/2008  .............. B01J 19/12
EP         0259163 A2      3/1988
(Continued)

OTHER PUBLICATIONS

International Search Report for PCT/IN2010/000123.

*Primary Examiner* — David Isabella
*Assistant Examiner* — Leslie Lopez
(74) *Attorney, Agent, or Firm* — The PL Law Group, PLLC

(57) ABSTRACT

A flexible magnetic membrane based actuation system comprising magnetic nanoparticles loaded into a polymeric material such as polyurethane and adapted to actuation of to and fro pumping motions of the membrane under application of magnetic field on the magnetic nanoparticles loaded membrane. More particularly, the present invention is directed to the said nanoparticles-loaded polyurethane magnetic membrane based actuation system adapted to function as displacement membrane for various activities requiring such to and fro motion. The magnetic membrane actuation is adapted to be controlled using electronic equipments to regulate the rate, force and frequency of displacement pulses. The magnetic membrane is thus capable of providing a simple, bio-compatible and cost effective means for displacement/mechanical work to assist functioning of various gadgets/medical devices including function as an artificial support system for heart, non-responsive diaphragm or a non-responsive sphincter, and thus capable of wide industrial applications.

2 Claims, 10 Drawing Sheets

Figure 1:
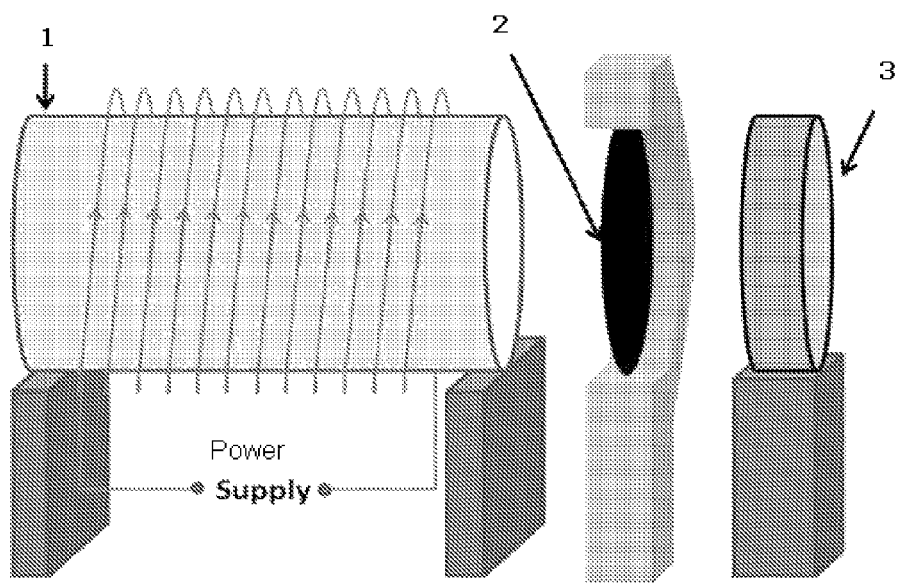

(52) U.S. Cl.
CPC ......... *F04B 43/043* (2013.01); *A61M 1/1037* (2013.01); *A61M 2205/3515* (2013.01)

(56) References Cited

U.S. PATENT DOCUMENTS

| | | | |
|---|---|---|---|
| 4,662,358 A * | 5/1987 | Farrar et al. | 600/16 |
| 4,918,383 A | 4/1990 | Huff et al. | |
| 5,498,228 A | 3/1996 | Royalty et al. | |
| 5,599,380 A | 2/1997 | Koros | |
| 6,099,460 A * | 8/2000 | Denker | 600/17 |
| 6,409,656 B1 | 6/2002 | Sangouard et al. | |
| 6,476,113 B1 | 11/2002 | Hiles | |
| 6,667,360 B1 | 12/2003 | Ng et al. | |
| 2002/0156339 A1 | 10/2002 | Kim | |
| 2006/0142632 A1* | 6/2006 | Meretei | 600/12 |
| 2007/0027460 A1* | 2/2007 | Case et al. | 606/151 |

FOREIGN PATENT DOCUMENTS

| | | |
|---|---|---|
| EP | 0304868 A2 | 3/1989 |
| EP | 2 133 106 A1 | 12/2009 |
| WO | WO0061227 A1 | 10/2000 |
| WO | WO 2008/106928 A2 | 9/2008 |

* cited by examiner

FLEXIBLE MAGNETIC MEMBRANE BASED ACTUATION SYSTEM AND DEVICES INVOLVING THE SAME

CROSS REFERENCE TO RELATED APPLICATIONS AND CLAIM OF PRIORITY

This patent application is a National Phase application under 35 U.S.C. §371 of International Application No. PCT/IN2010/000123, filed on Mar. 3, 2010, entire contents of which are incorporated herein by reference.

FIELD OF THE INVENTION

The invention relates to flexible polymeric membrane based actuation system and, in particular, to magnetic membranes comprising magnetic nanoparticles-loaded polyurethane magnetic membrane based actuation system adapted for magnetic and/or mechanical functions under attraction/influence of at least two external magnetic fields and thus capable of functioning as a displaceable membrane favouring use in various devices such as artificial cardiac support device or supporting a non-responsive diaphragm or a non-responsive sphincter or like applications. Advantageously, said displaceable magnetic nanoparticle-loaded flexible polymeric membrane based magnetic actuation system is adapted to providing to and fro controlled motion of the magnetic membrane adapted to assist pumping action based operating purposes and the like. Importantly, the characteristic magnetic and mechanical strength as well as pumping efficiency of the flexible membrane based actuation system is thus capable of providing a simple, biocompatible and cost effective means preferably for medical appliances for impaired heart or a non-responsive diaphragm facilitating the breathing or a non-responsive sphincter facilitating the discharge of urine/fecal subjects from human body. Thus such nanoparticles loaded flexible magnetic membrane based actuation system for said desired pumping action can be suitably applied for pumping fluids including suction of unwanted fluids in micro fluidics as a fluid based remotely controlled switch, means effecting the movement of paralyzed diaphragmatic muscle adapted to aid in the breathing of patient with phrenic paralysis, or for emptying of the urinary bladder in paralytic patients and artificial sphincters. The magnetic nanoparticles-loaded polyurethane magnetic membrane based actuation system of the invention is thus directed to provide a simple and cost effective displacement/mechanical work capable of assisting functioning of various medical/artificial support devices requiring any periodic displacement motion for operation and thus capable of wide applications in bio-medical appliance industry, research laboratories and the like.

BACKGROUND ART

Polymeric membranes are well known and used for variety of applications such as gas separation membranes, probing assemblies involving flexible membrane structures and similar applications.

To manufacture such polymeric membranes, a wide range of materials are used which include polyamides, polyimides, polyesters, polycarbonates, copolycarbonate esters, polyethers, polyetherketones, polyetherimides, polyethersulfones, polysulfones, polyvinylidene fluoride, polybenzimidazoles, polybenzoxazoles, polyacrylonitrile, cellulosic derivatives, polyazoaromaties, poly(2,6-dimethylphenylene oxide), polyphenylene oxides, polyureas, polyurethanes, polyhydrazides, polyazomethines, polyacetals, cellulose acetates, cellulose nitrate, ethyl cellulose, styrene-acrylonitrile copolymers, brominated poly(xylylene oxide), sulfonated poly(xylylene oxide), tetrahalogen-substituted polycarbonates, tetrahalogen-substituted polyesters, tetrahalogen-substituted polycarbonate esters, polyquinoxaline, polyamideimides, polyamide esters, polysiloxanes, polyacetylenes, polyphosphazenes, polyethylenes, polyphenylenes, poly(4-methylpentene), poly(trimethylsilylpropyne), poly(trialkylsilylacetylenes), polyureas, polyurethanes, and so-called ladder polymers, blends thereof, copolymers thereof; substituted materials thereof, and the like. It is further anticipated that polymerizable substances, that is, materials which cure to form a polymer, such as vulcanizable siloxanes and the like, may be suitable for making gas separation membranes.

U.S. Pat. No. 5,599,380 relates to polymeric composite or asymmetric gas separation membranes, particularly, polymeric gas separation membranes in which the morphology of the membrane is designed to increase the entropic selectivity effects of the membrane; and a process for the fabrication of such membranes.

A membrane probing assembly, for example, is exemplified by the device shown in Rath European Patent Pub. No. 259,163A2. This device has the central portion of the sheet-like membrane mounted directly against a rigid support. This rigid support, in turn, is connected by a resilient member comprising an elastomeric or rubber block to the main body of the assembly so that the membrane can tilt to match the tilt of the device. Huff (U.S. Pat. No. 4,918,383) shows a closely related device wherein radially extending leaf springs permit vertical axis movement of the rigid support while preventing it from tilting so that there is no slippage or "misalignment" of the contact bumps on the pads and further so that the entire membrane will shift slightly in the horizontal plane to allow the contacts to "scrub" across their respective pads in order to clear surface oxides from these pads. The test probe system is directed to providing an oxide-abrading scrubbing motion to scrub the contacts residing on a membrane probe card. The membrane used is simply stated to be stretchable.

A second conventional form of membrane probing assembly is exemplified by the device shown in Barsotti (European Patent Pub. No. 304,868A2). This device provides a flexible backing for the central or contact-carrying portion of the flexible membrane. In Barsotti, the membrane is directly backed by an elastomeric member and this member, in turn, is backed by a rigid support so that minor height variations between the contacts or pads can be accommodated. It is also possible to use positive-pressure air, negative-pressure air, liquid or an unbacked elastomer to provide flexible backing for the membrane, as shown in Gangroth U.S. Pat. No. 4,649,339.

It is also known in the art to provide magnetically active flexible polymers. U.S. Pat. No. 6,476,113 relates to thermosetting and thermoplastic elastomers having magnetic filler packed within the elastomeric matrix and capable of being aligned and energized, before, during or after the molding of the elastomer. The magnetically-filled elastomers therefore provide useful permanent magnetic fields which being physically soft. The magnetic filler is aligned within the elastomeric matrix and energized by subjecting the magnetically-filled elastomer to magnetic energy before, during and/or after molding of the magnetically-filled elastomer. Vibration dampening devices employing elastomers and, more particularly, the magnetically-filled elastomers of U.S. Pat. No. 6,476,113 are also provided. In this invention the metallic or alloy particles are embedded in the elastomeric membrane adapted to be magnetized.

U.S. Pat. No. 6,667,360 is a patent entitled 'Nanoparticle-filled polymers' discloses polymer nanocomposite comprising: a. about 50-99 weight % polymer resin and b. about 1-50 weight % crystalline nanoparticles having particle size from about 1 nm to less than about 100 nm; a narrow particle size distribution and a chemically clean surface, said nanoparticles consisting of one or more metals, one or more metal oxides, one or more metal nitrides, one or more metal carbides, one or more metal sulfides, one or more metal fluorides, one or more metal chlorides, or a mixture thereof, wherein said polymer resin is chosen from the group consisting of: epoxy, polycarbonate, silicone, polyester, polyether, polyolefin, synthetic rubber, polyurethane, nylon, polystyrene, polyphenylene oxide, and polyketone and copolymers and blends thereof. Such filled polymers are directed to achieve improved mechanical/chemical properties, including scratch resistance, increased modulus while maintaining good ductility, also such polymers having improved dimensional stability for intended application as optical lens, epoxy-fiberglass composites, magnetic tape, paints and the like.

Thus the above mentioned state of the art reveals some applications and uses of electrometric membranes for various end use/applications. There is however no magnetic actuation of the membrane as an actuation system being targeted by any of such said prior arts.

It is also well known in the treatment of cardio thorasic ailments/disorders, that there is a lot of interest world wide on developing artificial hearts for a variety of purposes which involve artificially supporting the functioning of the heart by way of some external pumping actions.

1. For temporary support as a bridge to recovery of the native heart which is temporarily malfunctional.
2. For more long-term support, as a bridge to transplantation, to allow patients listed for heart transplant to survive till a suitable donor heart is found.
3. Long term support for an indefinite period, so called "destination therapy".

It is also known in related art that in most of the several pulsatile pumps which are currently available, a biocompatible polyurethane membrane is used whose displacement causes the blood to be shifted and pumped. This polyurethane is typically displaced, either pneumatically or by using an electric current. In both instances, when the pump itself is implanted inside the human body, the cables, enabling the said displacement either actuated electrically or pneumatically, have to traverse the skin barrier to enter the body and come out, leading to inevitable, high rate of infectious complications.

Thus the existing pulsating artificial heart pumps, generally, employing pneumatic, electrical or magnetic means for their functioning suffered from the limitations wherein the conductor for carrying the air or electrical current has to cross the skin barrier physically needing external source of power supply and this lead to complications due to infections. There has thus been a need in the art for driving artificial heart support systems involving preferably magnetic actuation, providing the energy transferred from outside the body without such crossing of the skin barrier or any physical connectivity of energy source through the body, thus avoiding chances of infection and related complications.

Several attempts have been made in this direction to develop an artificial heart pump made of biocompatible material ensuring desired reliable functional performance as an alternative to conventional pneumatic or electrically operated heart assist, device to be replaced with magnetically actuated cardiac assisting device to provide total support for different kinds of heart ailments.

U.S. Pat. No. 5,498,228 is a prior patent by Royalty et al. which discloses an 'electromagnetic bi-ventricular assist device'. It basically consisted of a magnetic mat, an assembly of electromagnet, a transducer and a control circuit to regulate the compressive force applied to the heart. The magnetic mat, is a permanent magnet made from a flexible ferromagnetic material like samarium-cobalt, neodymium-iron or any superconducting material and coated with polyvinyl chloride or polytetrafluoroethylene (PTFE) so that the exterior surface of the mat does not react with blood, tissues or organs. The mat can be positioned between heart and the pericardium to facilitate compression action of the heart/ventricle or selectively disposed anterior to both the heart and the pericardium. The mat is installed at site supported by strong and flexible mono-filament surgical threads for holding the mat with the rib cage or sternum.

The magnetic mat of the above cited prior art also involves an electromagnetic assembly mounted externally on the chest to control the desired degree of compression by said electromagnetic device which generates and discontinues alternately, electromagnetic field of desired intensity, in order to alternately compress the mat against vertebral body and then permit the mat to relax, thereby assisting the pumping function of the heart by applying compressive force only. A transducer attached to the electromagnetic assembly on the side opposite to the chest by rigid harness. The harness may include shoulder straps to prevent undesired vertical movement of the electromagnetic assembly when a person is in upright position. The transducer is the part of a feed-back control loop. When the electromagnetic assembly generates an electromagnetic field to repel the mat, an equal and opposite force is applied to the electromagnetic assembly itself, thus repelling the assembly away from the chest. Thus the electromagnetic field so generated by the assembly leads to compression of the pressure transducer in between the electromagnetic assembly and the harness. The transducer senses this compressive pressure and gives a voltage output, which is proportional to this pressure. A control circuit receives the signal generated by the transducer and controls the intensity of the electromagnetic field generated by the electromagnetic assembly as a function of the electromagnetic signal. This enables the control circuit to effectively control the degree to which the mat compresses the heart.

U.S. Pat. No. 6,099,460 discloses that a heart may be artificially contracted to pump blood by separate electromagnets on the exterior surface to the heart and by implanting another electromagnet inside any chamber of the heart and allowing controlled electric current through said selectively disposed electromagnet to attract each other in pair so as to co-operatively actuate pumping of the blood out of a heart chamber by the attraction of the electromagnets due to the magnetic fields created.

WO 00/61227 states that a heart can be artificially contracted to pump blood from the heart chamber using an artificial device that employs an electromagnetic force. The device includes electromagnetic coils attached to the ribs and permanent magnets placed adjacent to the electromagnetic coils. When a direct electric current is applied to the electromagnetic coils, the magnetic fields from the electromagnets and the permanent magnets interact so that the permanent magnets are repelled so as to apply contraction force causing blood pumping assistance for the heart.

U.S. Pat. No. 6,604,529 teaches about aiding the compression and relaxation of a heart chamber using ferromagnetic and diamagnetic pellets inserted into the anterior and posterior walls of the chamber. The pellets are inserted into the myocardial walls of the heart chamber by means of a delivery catheter. Electromagnetic fields, which are used to push and pull the pellets to compress and relax the hear chamber, are cyclically generated by electromagnetic field generators positioned on a patient's chest and back wall.

It is however experienced that the above state of the art of artificial heart pumping gadgets presently available and in use have some inherent complexities. The U.S. Pat. No. 5,498,228 involved placing the magnetic mat in between the heart and the pericardium requiring removal of a large amount of body tissues from this region by complex surgery. Further, the attachment of the magnetic mat/electromagnetic coils with the rib cage by flexible mono-filament threads also involves risks of being torn apart. Moreover, such magnetic mat/magnetic field due to electromagnetic attraction being compressive type, the external electromagnet assembly can only compress the heart to push out blood through the arteries but it cannot expand on its own to come back to its diastolic mode. Thus such a device is not capable of assisting heart ailments needing support for diastolic process too. Although U.S. Pat. No. 6,604,529 is directed to electromagnetic system that assist both systolic and diastolic ventricular function and that the electromagnetic assemblies are placed on chest and back wall, the insertion of ferromagnetic and diamagnetic pellets into the selective walls of the heart chamber is a very complex process and involve high cost and risk for implementing such process, affecting viability and easy adaptation to common heart patients at large.

Some of the most recently introduced cardiac assist devices in the art, are learnt to have used electric and pneumatic activation of a polyurethane membrane. Magnetic actuation to achieve consistent mechanical output as displacement pump has not yet been attempted or produced in a commercially viable form such as for cardiac assist and other organ disorder support purposes.

OBJECTS OF THE INVENTION

It is thus the basic object of the present invention to provide a flexible magnetic membrane based actuation system involving magnetic nanoparticles loaded polyurethane membrane adapted to perform magnetic or mechanical functions under influence of selective external magnetic field involving motion on either direction which can be adapted for variety of end uses/application involving such pumping action/support.

Another object of the present invention is directed to the provision of a flexible magnetic membrane based actuation system for displaceable pump system involving a low cost biocompatible displaceable membrane adapted to generate to and fro motion on either direction under magnetic action adapted for cooperative action to periodically activate any function based on such to and fro motion of the magnetic membrane to assist/support functioning and/or functional disorder for human body organs/systems including artificial heart support system.

A further object of the present invention is directed to a flexible magnetic membrane based actuation system adapted for magnetic and mechanical function by controlled magnetic field adapted for operation with electronic control equipments for regulated and controlled exposure of the membrane to magnetic field for the required periodic to and fro motion of the membrane.

A further object of the present invention is directed to a flexible magnetic membrane based actuation system adapted for magnetic and mechanical function by application of controlled magnetic field wherein said membrane is obtained of variety of shape and sizes depending upon the end use requirement.

A further object of the present invention is directed to a flexible magnetic membrane based actuation system adapted for controlled magnetic and mechanical function by selective disposition of the magnetic nanoparticles in the membrane.

A further object of the present invention is directed to a flexible magnetic membrane based actuation system adapted for magnetic and mechanical function by controlled magnetic field adapted for assisting various appliances under magnetic actuation of the membrane.

A still further object of the present invention is directed to a magnetic nanoparticles loaded flexible magnetic polyurethane membrane used in said actuation system adapted for assisting various bio-medical appliances under magnetic actuation which would be adapted to respond to even weak magnetic fields.

It is a further object of the present invention to provide a flexible magnetic membrane based displacement pump support system adapted for artificial heart support which would be adapted to interact for desired pumping action for supporting an artificial heart.

Another object of the present invention is directed to a flexible magnetic membrane based displacement pump support system adapted for artificial heart support as cardiac assist/support device for partially impaired heart or replacing a totally failing heart functioning as low cost displacement pump using magnetically actuated flexible magnetic nanoparticle loaded polymeric membrane.

A further object of the present invention is directed to a magnetically displaceable nanoparticle loaded membrane based displacement pump support system adapted for artificial heart support/cardiac assist device which would avoid the need for passage of any conductor carrying compressed air or electrical current to cross the skin barrier of the patient and thus eliminating possibilities of any infection and related complications.

A still further object of the present invention directed to a magnetically displaceable nanoparticle loaded membrane based displacement pump system adapted for artificial heart support directed to perform cardiac function capable of both systolic and diastolic movements of heart, under the action of a selective magnetic field.

A still further object of the present invention directed to a magnetically displaceable nano particle loaded membrane based displacement pump system adapted for use in cardiac or other organic system support functions wherein electronic control equipments are used for controlled electrical energizing of the electromagnet to create/maintain appropriate strength of magnetic field at desired pulse rate such as the magnetic field force, in association with permanent magnets, leads to displacement pumping or back and forth motion of magnetic membrane to favour-desired assistance in heart function.

A still further object of the present invention is directed to an artificial medical grade bio-compatible nanoparticles loaded membrane based displacement pump system for artificial heart support system or the like, involving a magnetic nanoparticles loaded magnetic PU membrane which would be low cost and reliable device and easily installed and operated.

A still further object of the present invention is directed to a displaceable membrane based cardiac support device with possibility for characterization of the magnetic properties and mechanical strength to achieve desired precise tailoring of the magnetic properties of the membrane, required for supporting an ailing heart.

A still further object of the present invention is directed to a displaceable membrane based actuation pump support system adapted for assisting impaired heart function adapted for providing regulated actuation including the rate, force and 'R' wave triggering for co-coordinating with desired cardiac activity or to act as Total Artificial Heart (TAH).

A still further object of the present invention is directed to a magnetically displaceable nanoparticles loaded polyurethane magnetic membrane based actuation system adapted to support impaired respiratory function with phrenic paralysis, wherein a magnetic nanoparticle embedded polyurethane membrane sutured onto a paralysed diaphragm is activated by an electromagnet and triggered to coincide with the initial respiratory effort, so that the diaphragm can move down like normal, facilitating the patient to breathe normally. A still further object of the present invention is directed to a magnetically displaceable nanoparticles loaded polyurethane magnetic membrane based actuation system adapted to assist emptying of the urinary bladder in paralytic patients with incompetence of normal sphincters and/or ineffective artificial sphincters.

SUMMARY OF THE INVENTION

Thus, according to the basic aspect of the present invention there is provided a flexible magnetic membrane based actuation system comprising:
 a flexible polymeric membrane loaded with magnetic nanoparticles;
 an electromagnet and permanent magnet (s) adapted to generate magnetic force;
 said flexible polymeric membrane adapted to selectively vary position of the membrane based on direction of exposure to any external magnetic field.

In the said flexible magnetic membrane based actuation system of the invention wherein the polymeric membrane comprise of a polymeric material.

Another aspect of the present invention is directed to said flexible magnetic membrane based actuation system, wherein said polymeric material comprises of a medical grade biocompatible polymeric material such as polyurethane.

A further aspect of the present invention is directed to a flexible magnetic membrane based actuation system, wherein said magnetic nanoparticles comprise $Fe_3O_4$, cobalt or any other superparamagnetic nanoparticles having extremely large magnetic moment and large susceptibility to magnetic fields with sizes varying between 1 nm to 100 nm, preferably $Fe_3O_4$ of size 20-30 nm.

A still further aspect of the present invention is directed to a flexible magnetic membrane based actuation system comprising said nanoparticles provided into biospan segmented polyurethane.

A still further aspect of the present invention is directed to a flexible magnetic membrane based actuation system, wherein said magnetic nanoparticles are loaded in the polymer membrane such as to form a stable dispersion.

According to yet another aspect of the present invention is directed to the said flexible magnetic membrane based actuation system, wherein the same is adapted for to and fro displacement motion when exposed to two opposing magnetic fields for mechanical working purposes.

A still further aspect of the present invention is directed to the said flexible magnetic membrane based actuation system, which is flexible and adapted to respond to even weak magnetic fields.

A still further aspect of the present invention is directed to a flexible magnetic membrane based actuation system, wherein said means to generate magnetic force comprises electromagnet means and permanent magnet including rare earth magnets preferably NdFeB, SmCo and the like.

According to an important aspect, the present invention is directed to the said flexible magnetic membrane based actuation system, comprising a function generator adapted for supplying periodic electrical signal to the electromagnet such that the electromagnet is adapted to produce periodic magnetic force sufficient to, release the said membrane periodically from its usual disposition based on its attraction towards the said permanent magnet.

A still further aspect of the present invention is directed to a flexible magnetic membrane based actuation system, wherein the frequency of the input electric signal to the electromagnet is synchronized with the desired periodicity of the to and fro motion of the membrane desired.

A still further aspect of the present invention is directed to a flexible magnetic membrane based actuation system comprising electronic means adapted for regulating the actuation including the rate, force and "R" wave triggering for coordinating with the desired end activity based on the to and fro motion of the membrane.

According to yet another aspect, the present invention is directed to a device adapted for reciprocating to and fro pumping related applications comprising the said flexible magnetic membrane based actuation system cooperatively connected to operative components for the said desired pumping action.

Also in the said device, according to the present invention, wherein said operative components for said desired pumping action selectively include means for pumping fluids including suction of unwanted fluids in micro fluidics as a fluid based remotely controlled switch, means effecting the movement of paralyzed diaphragmatic muscle adapted to aid in the breathing of patient with phrenic paralysis, means adapted for emptying of the urinary bladder in paralytic patients and artificial sphincters.

A still further aspect of the present invention is directed to a displacement pump support system adapted for artificial heart support comprising:
a housing having an inlet for the flow of blood inside and an outlet to favour the blood out of said housing;
a magnetic nanoparticle loaded polyurethane membrane disposed within the said housing;
a permanent magnet adapted to be disposed inside the body and in proximity to said housing such that it enables maintaining a desired usual attracted disposition of the said nanoparticle loaded membrane with respect to said permanent magnet in the said housing; and
an electromagnet means adapted to be suitably placed outside the body which can be selectively energized to effect a required intermittent displacement of the membrane from its said usual disposition in the housing such that in the process a pumping action is generated to take in and drive out the blood from the housing and in the process facilitate the required artificial heart support.

A still further aspect of the present invention is directed to said displacement pump support system adapted for artificial heart support, wherein the said electromagnet is operatively connected to a function generator for supplying periodic electrical signal to the electromagnet such that the electromagnet produces a dc magnetic field and thereby produce the desired back and forth motion of the magnetic membrane for said artificial pumping support for the heart.

In said displacement pump support system of the invention adapted for artificial heart support, wherein the said back and forth periodic motion of the membrane is adapted for supporting the systolic and diastolic movement of the heart.

A still further aspect of the present invention is directed to said displacement pump support system adapted for artificial heart support wherein, frequency of the input electric signal to the electromagnet is adapted to synchronize with the desired heart beat.

Advantageously also said displacement pump support system adapted for artificial heart support comprising electronic means adapted for regulating the actuation including the rate, force and "R" wave triggering for coordinating with inherent cardiac activity.

A still further aspect of the present invention is directed to said displacement pump support system adapted for artificial heart support comprising
  said magnetic nanoparticle loaded polymeric membrane provided in a polymeric housing having an inlet and outlet for receiving and pumping the blood from and into the body, said inlet and outlet being guarded by one way valve means;
  said electromagnet adapted for wearing outside the body and disposed opposite to the permanent magnet which is adapted to be placed on the wall of said polymeric casing such that the magnetic membrane in said casing is disposed there between the electromagnet and the permanent magnet; and
  said electromagnet operatively connected to said function generator for supplying periodic electrical signal to the electromagnet such that the electromagnet produces a dc magnetic field and thereby produces the desired back and forth motion of the magnetic membrane for said artificial pumping support for the blood in contact with said displaceable membrane.

According to yet another aspect of the present invention directed to said displacement pump support system adapted for artificial heart support wherein, the said electromagnet is adapted to operate based on dc input supply such that when there is no current through the electromagnet, the magnetic membrane remains attracted by the permanent magnet and as the dc supply is increased through the electromagnet, the magnetic field generated by the electromagnet increases and the membrane is pulled and when it overcomes the magnetic pull of the permanent magnet the membrane is displaced towards the electromagnet and again when the current through the electromagnet is reduced and made zero the permanent magnet is adapted to pull back the membrane for its desired to and fro displacement motion.

A still further aspect of the present invention is directed to a displacement pump support system adapted for artificial heart support wherein, the electromagnet is fed with controlled current manually or by a pulsed shape electric signal generated by a function generator.

Another aspect of the present invention is directed to an artificial heart comprising comprising:
a support pumping system for blood circulation like that in the various chambers of a heart comprising:
  a housing having an inlet for the flow of blood inside and an outlet to favour the blood out of said housing;
  a magnetic nanoparticle loaded polyurethane membrane disposed within the said housing;
  a permanent magnet adapted to be disposed inside the body and in proximity to said housing such that it enables maintaining a desired usual attracted disposition of the said nanoparticle loaded membrane with respect to said permanent magnet in the said housing; and
  an electromagnet means adapted to be suitably placed outside the body which can be selectively energized to effect a required intermittent displacement of the membrane from its said usual disposition in the housing such that in the process a pumping action is generated to take in and drive out the blood from the housing adapted to facilitate the circulating motion of blood as in an human heart,
  said support system operatively connected to an artificial heart with said chambers for circulating blood.

According to yet another aspect, the present invention is directed to a kit adapted to function as an artificial heart support mechanism comprising:
  a magnetic nanoparticles loaded membrane adapted to be selectively disposed within the heart;
  a permanent magnet adapted to be disposed inside the body and in proximity such that it enables maintaining a desired usual attracted disposition of the said nanoparticle loaded membrane with respect to the said permanent magnet in the said housing; and
  an electromagnet means adapted to be suitably placed outside the body which can be selectively energized to effect a required intermittent displacement of the membrane from its said usual disposition such that in the process a pumping action is generated to take in and drive out the blood from the heart chambers and facilitate the circulating motion of blood as in an human heart.

A still further aspect of the present invention is directed to the said kit adapted to function as a support for paralyzed diaphragm and facilitate the breathing process comprising:
  a magnetic nanoparticles loaded membrane adapted to be sutured or otherwise secured onto a paralyzed diaphragm;
  an electromagnet means adapted to generate intermittent magnetic force to favour regulated to and fro motion of the said membrane secured to the said diaphragm and in the process facilitate the breathing.

A still further aspect of the present invention is directed to the said kit adapted to function as support for non-responsive sphincters to facilitate controlled discharge of urine/fecal matters comprising:
  a magnetic nanoparticle loaded membrane adapted to be sutured or otherwise secured onto a non-responsive sphincters;
  an electromagnet means adapted to generate intermittent magnetic force to favour regulated to and fro motion of the said membrane secured to said non-responsive sphincters and in the process facilitate the operation of the non-responsive sphincters.

A still further aspect of the present invention is directed to said kit comprising a function generator adapted for supplying periodic/regulated electrical signals to the electromagnet such that the electromagnet is adapted to produce regulated magnetic force support to pull and release said paralytic diaphragm or said non-responsive sphincter to thereby favouring its function for breathing or discharge of urine/fecal matters respectively.

According to yet another aspect of the present invention is directed to a process for the manufacture of the flexible magnetic membrane for use as flexible magnetic membrane based actuation system comprising:

mixing the magnetic nanoparticles in gel type biocompatible polymeric material to obtain an uniform mixture;

providing the above mix of the polymeric material with the magnetic nanoparticles on a selective substrate based on the shape of the membrane to be obtained and heating such as to provide the said flexible magnetic membrane.

A still further aspect of the present invention is directed to said process for the manufacture of the flexible magnetic membrane comprising:

mixing the magnetic material with gel type polyurethane with constant stirring to obtain uniform mixture;

providing the above mix of polyurethane with the magnetic nanoparticles on a selective substrate based on the desired shape of the membrane;

heating to drive off the dimethylacetamide (DMAc) present in the polyurethane and finally obtain the said flexible magnetic membrane.

A still further aspect of the present invention is directed to said process for the manufacture of the flexible magnetic membrane wherein said step of heating comprises an initial heating in the temperature range of 30-35° C. with ventilation followed by final heating at a temperature of 60° C. for ~ 24 hrs.

The present invention and its objects and advantages are described in greater details with reference to the following accompanying non limiting illustrative figures.

BRIEF DESCRIPTION OF THE
ACCOMPANYING FIGURES

Figure 2:
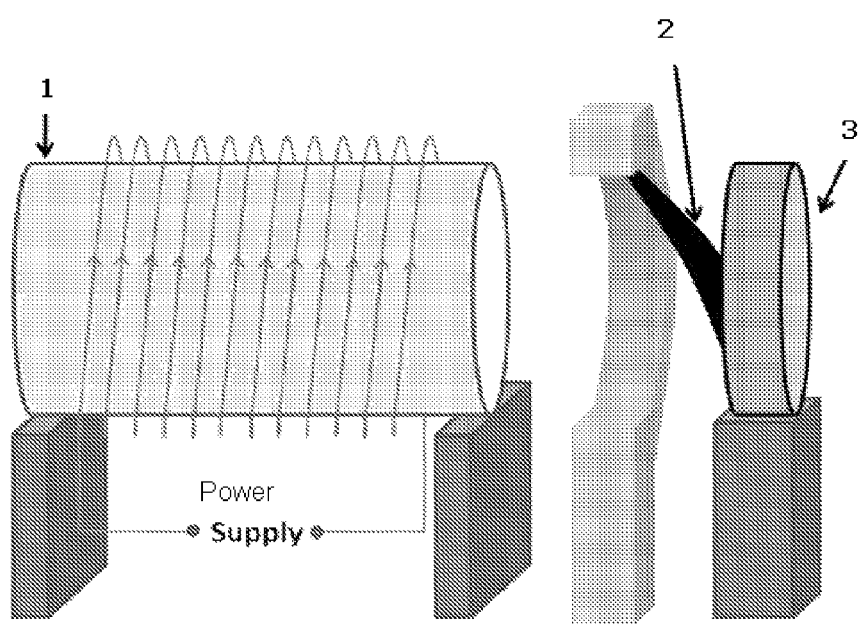
Figure 3:
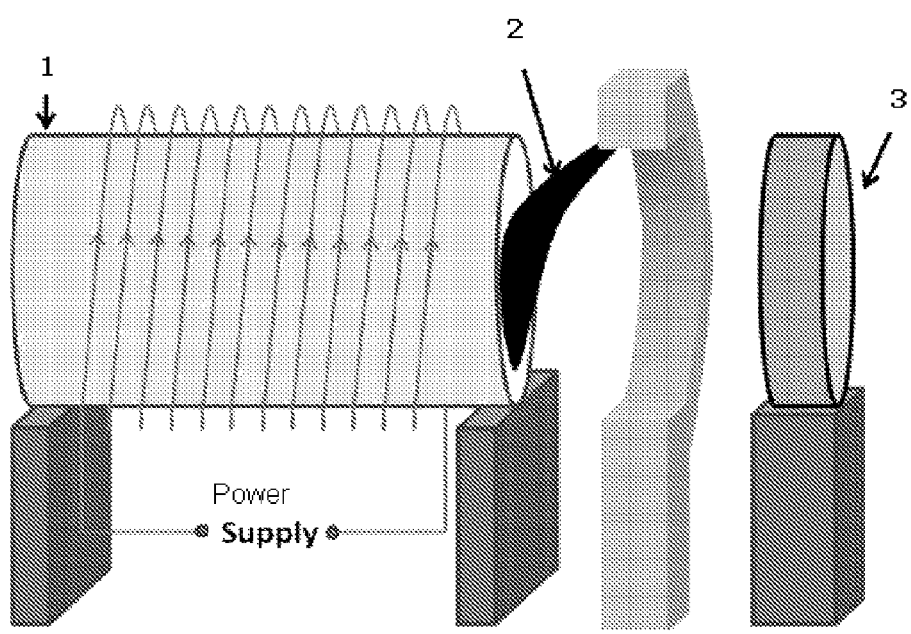
Figure 4:
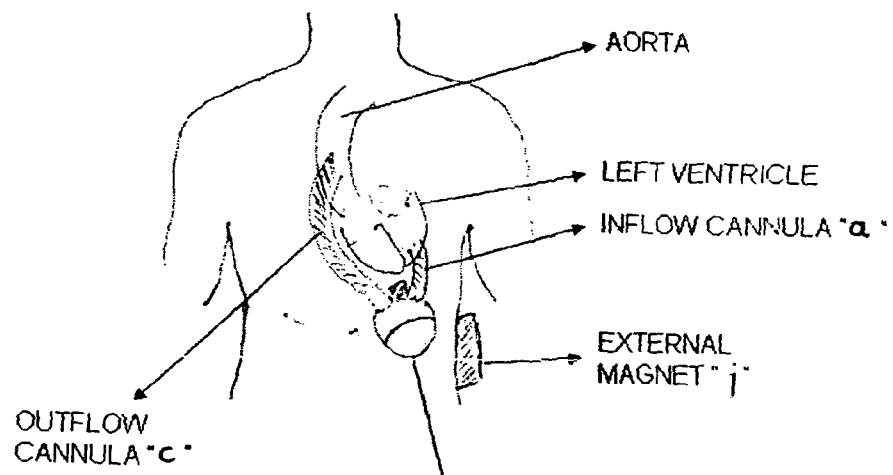
Figure 4:
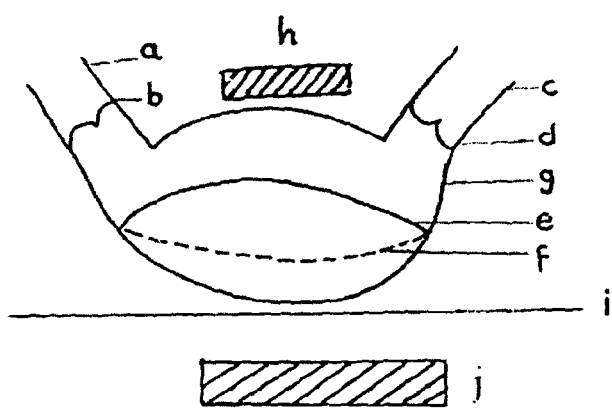

FIG. 1: is a schematic illustration of an experimental embodiment of the flexible magnetic membrane of the invention in its usual disposition;

FIG. 2: is a schematic illustration of the flexible magnetic membrane of FIG. 1 in the displaced disposition due to an attractive magnetic energy arising from the permanent magnets located at the right side of the said magnetic membrane;

FIG. 3: is a schematic illustration of the flexible magnetic membrane of FIG. 1 in the displaced disposition opposite to that in FIG. 2 due to attractive magnetic energy arising from the electromagnet located at the left side of the Figure;

FIG. 4: is a schematic diagram of an embodiment of displaceable membrane based actuation system of the present invention. The device shown in figure (below the first one) in enlarged form is the invention. It is a schematic diagram of disposition of the displaceable membrane based actuation system as a heart support system in the human body.

Figure 5:
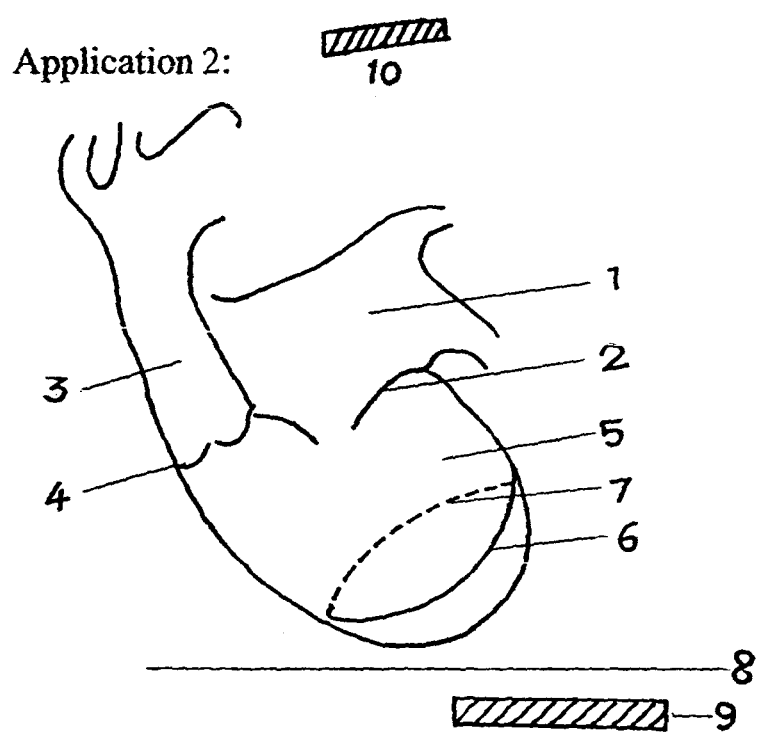

FIG. 5: is a selective configuration according to a preferred embodiment of the displaceable membrane based actuation system of the present invention comprising a magnetically actuated intra ventricular patch for imparting regional contractility to the heart.

Figure 6A:
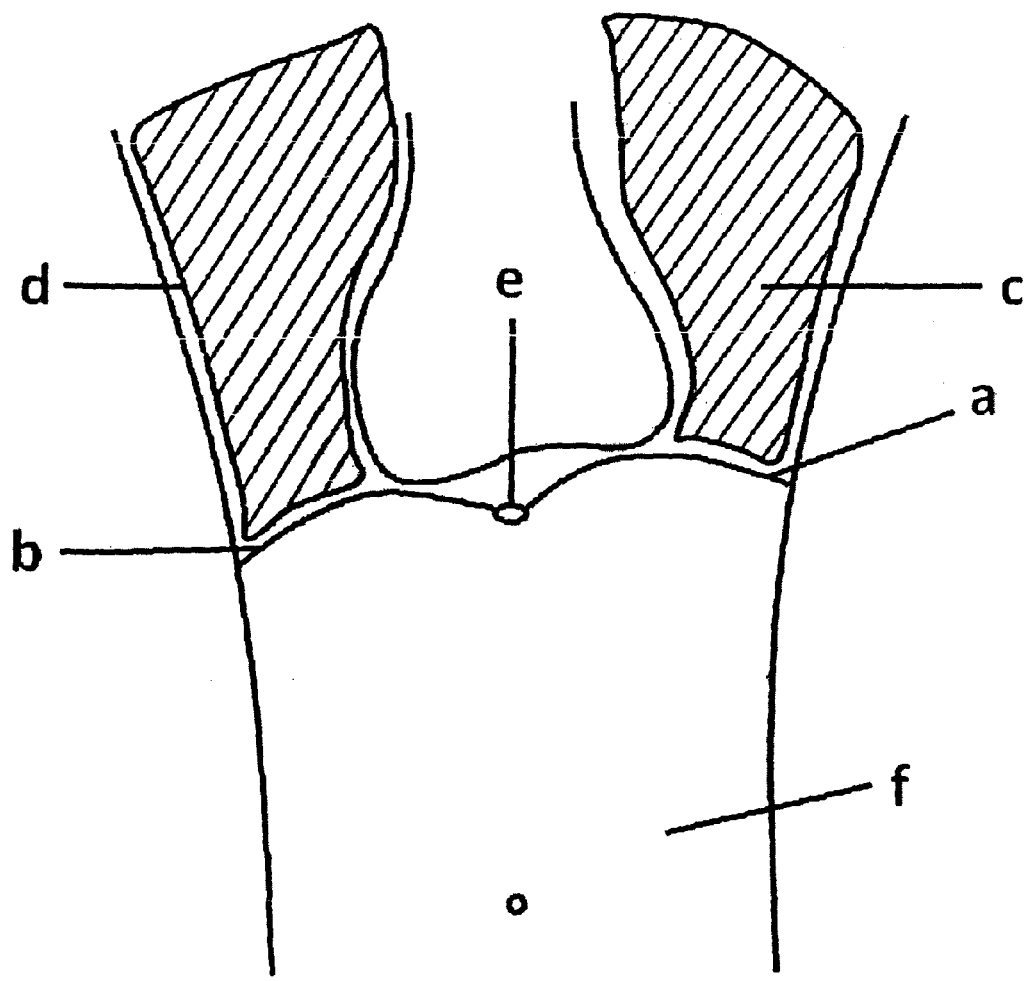

FIG. 6(a): is a schematic illustration of the anatomy of chest and abdominal portion showing the disposition of abdominal diaphragm having normal deflection, which facilitate the rhythmic respiration.

Figure 6B:
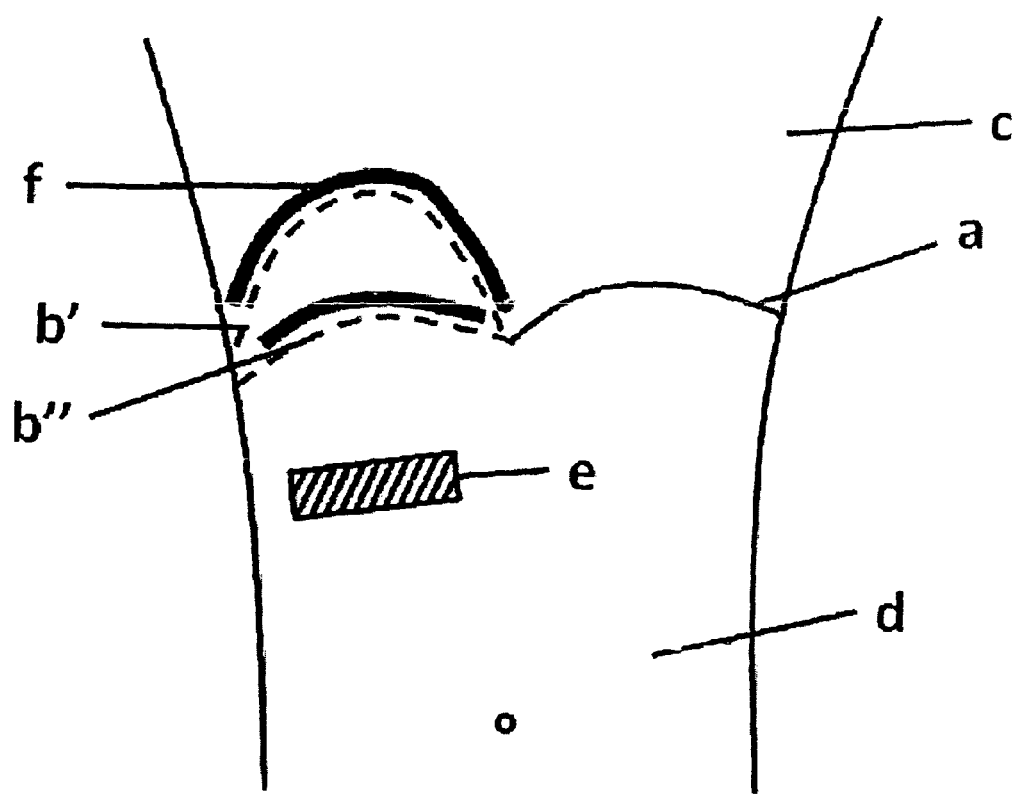

FIG. 6(b): is the schematic illustration of the viscera of abdominal cavity and chest wherein the paralyzed right dome of the abdominal diaphragm is assisted by the nanoparticles loaded magnetic membrane disposed on the right dome of the diaphragm affected with phernic paralysis and actuated by an electromagnet placed outside body wall.

Figure 7A:
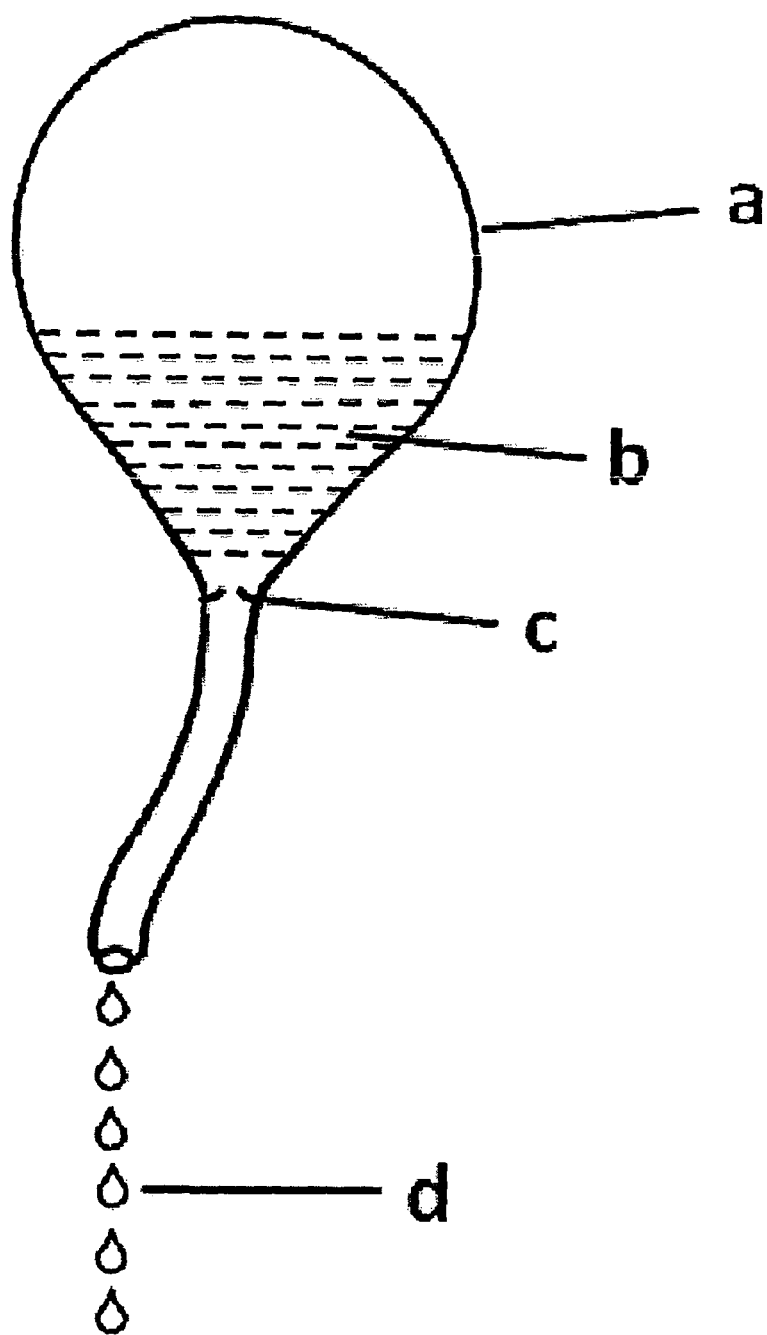
Figure 7B:
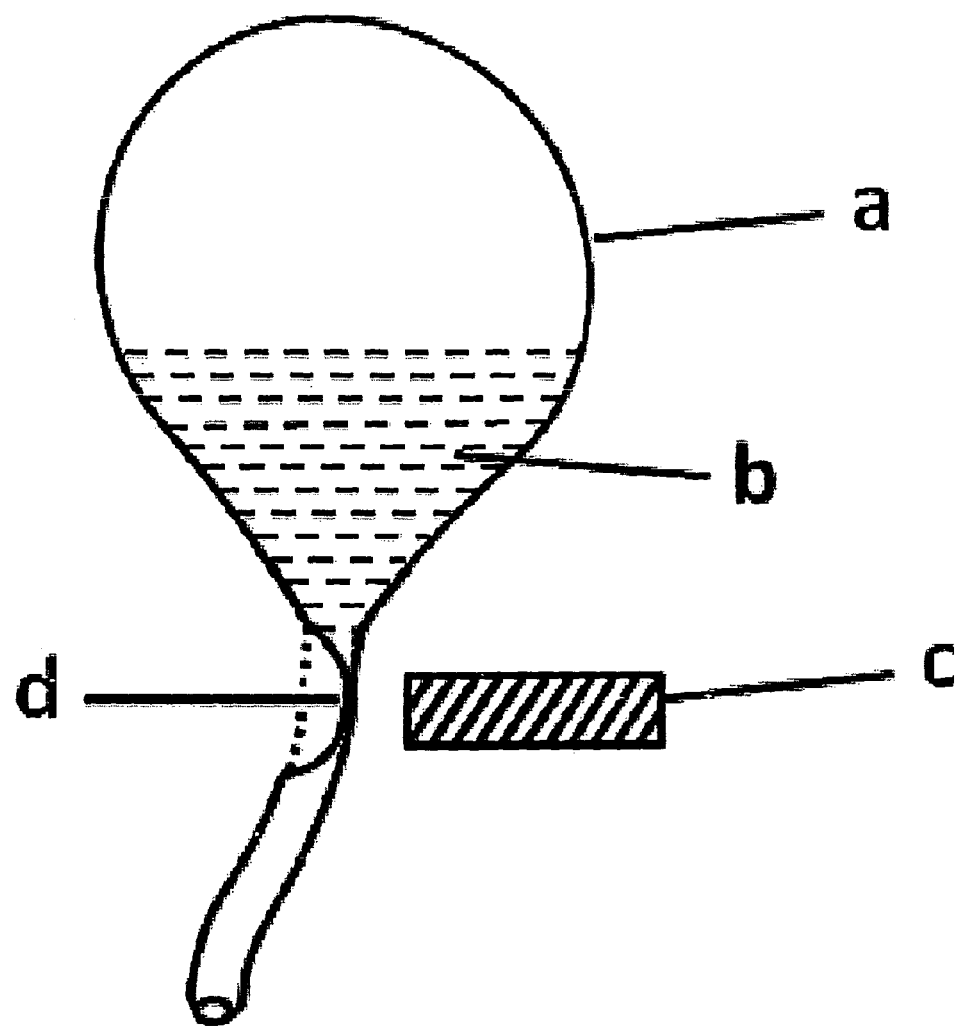
Figure 7C:
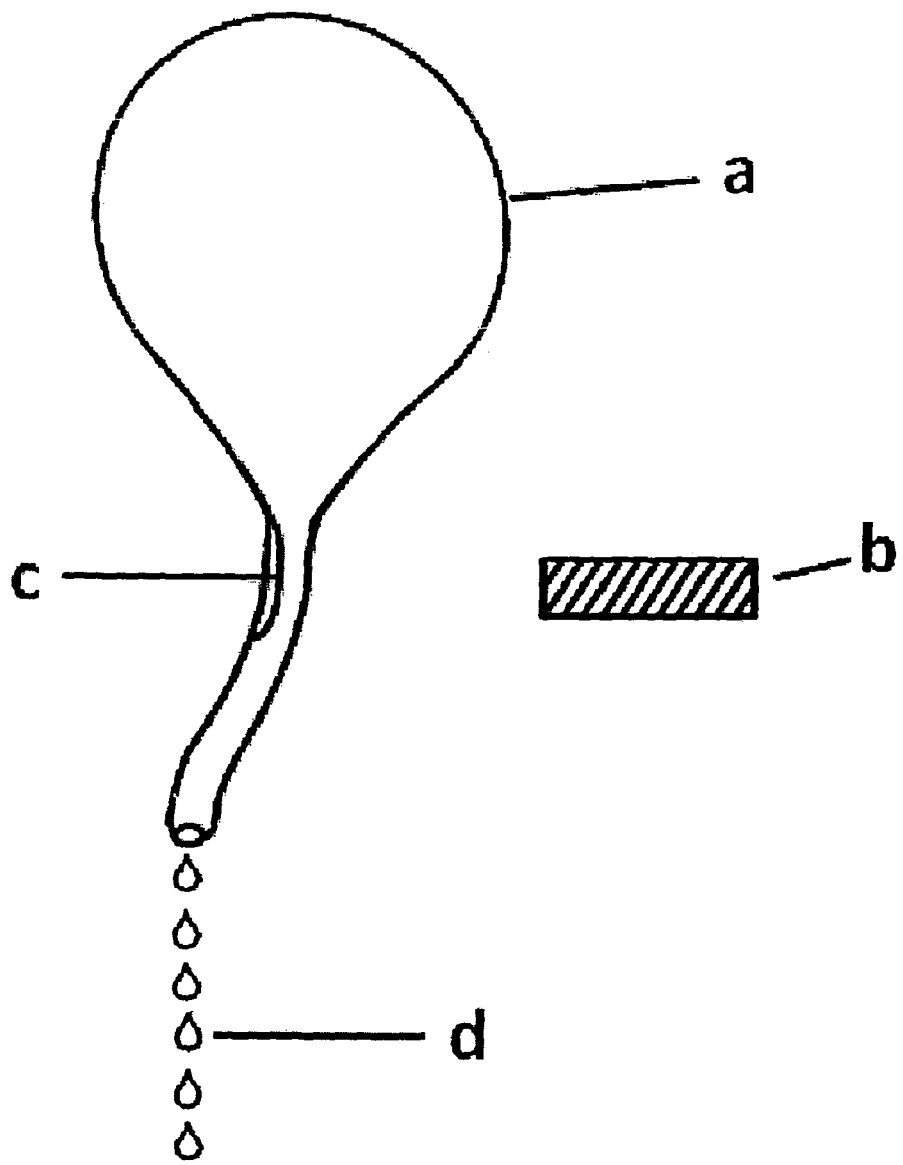

FIG. 7(a) to (c): is the schematic illustration of functioning of flexible magnetic actuation of nanoparticles loaded flexible polymeric membrane applied to assist ineffective sphincters to facilitate holding or discharging urine from the urinary bladder by electromagnetic actuation.

DETAILED DESCRIPTION OF THE
INVENTION WITH REFERENCE TO THE
ACCOMPANYING FIGURES

Reference is first invited to the accompanying FIG. 1 that shows the typical arrangement of a flexible polymeric magnetic membrane based actuation system wherein said membrane 2 is placed in between an electromagnet 1 and a permanent magnet 3 assembly by using suitable brass made membrane holder in a linear fashion. Suitable brass-made permanent magnet holder is also made for holding them so as to maintain the distance between the magnetic membrane 2 and the electromagnet 1 is set at selective gap for desired actuation. In this case, the force on the magnetic membrane 2 generated by the said electromagnet 1 cancels the resultant force due to the permanent magnets. Thereby, the magnetic membrane remains standstill.

The accompanying FIG. 2 shows an embodiment of the system according to the present invention where the flexible polymeric magnetic membrane 2 (of FIG. 1) is attracted towards the permanent magnet 3 assembly. In this case, the current through the electromagnet 1 is kept zero i.e. the electromagnet 1 is not applying any force on the magnetic membrane.2.

Reference is now given to the accompanying FIG. 3 that shows in the embodiment as of FIG. 3 wherein the flexible polymeric magnetic membrane 2 (as shown in FIG. 1) is attracted in a direction opposite to that described in FIG. 2. Such a situation can be achieved by passing an adequate current through the electromagnet,1, thereby, applying an opposing force on the magnetic membrane 2. When the magnetic force on the membrane 2 due to the electromagnet 1 overcomes that of the permanent magnet(s) 3, the magnetic membrane 2 is fully attracted by the electromagnet 1.

The detailed step by step description for the fabrication of the magnetic nanoparticles loaded flexible PU membrane according to the present invention is as follows:

1) Placing an empty glass beaker within an ice jacket.
2) Transferring the required amount of polyurethane from the sealed container (preserved at 4° C.) to the glass beaker.
3) Mixing the said magnetic nanoparticles with the gel type polyurethane with constant stirring to obtain a uniform mixture.
4) After stirring for a reasonable time, the mixture of polyurethane and the magnetic nanoparticles was transferred to a petri dish (a shallow glass dish with flat bottom surface) followed by immediate shaking to give a membrane like structure. The inner diameter of the Petri dish was chosen as per the required diameter of the desired membrane. The desired thickness of the membranes was controlled by the pouring the required amount of mixture of the products obtained at stage #3. For preparing a curved membrane a hemispherical hollow glass substrate is used.
5) Heating the Petri dish (containing the membrane material) at 30-35° C. with adequate ventilation. The elevated temperature is required to get rid off dimethylacetamide (DMAc) present in the supplied polyurethane.

6) A final heating at 60° C. for 24 hours or longer (depending on membrane thickness) is required to remove the final trace of DMAc.

The above figures and their descriptions thus clearly illustrate the magnetic nanoparticles loaded polyurethane (PU) based membrane adapted to generate- to and fro motion under the actuation of external magnetic field of selective strength, involving preferably a pair of magnets of desired strength one of which can be an electromagnet while the other one is a permanent magnet(s) selectively disposed on either sides of the magnetic membrane The electromagnet can be energized in a controlled manner through electronic control equipments to generate appropriate magnetic field strength such that the membrane move back and forth between the two magnets and thus providing the basic motion and attain the drive force similar to that of a displacement pump.

Thus above magnetic membrane of the invention can as illustrated above comprise magnetic nanoparticles loaded into a medical grade biocompatible polymeric material like polyurethane (PU).

Following the above magnetic nanoparticles based flexible membrane it is also possible to vary the end characteristics of the membrane by characterization of the magnetic properties and mechanical strength of a small representative piece of the magnetic nanoparticles loaded in the membrane.

From the above illustrations, we can observe that the nanoparticles form a stable dispersion although the nanoparticles are randomly distributed in the polymeric matrix.

This magnetic membrane of the invention is thus adapted such as to undergo the to and fro movements/displacement by two opposing magnetic fields of requisite field strength enabling possible reciprocating support functions in variety of devices.

The back and forth motion of the flexible magnetic membrane thus achieved can be utilized in various industrial applications/devices to carry out required mechanical work. The frequency of the input electric signal to the electromagnet can be synchronized with any specific frequency required to assist any device involving reciprocating and/or like displacement functions. Electronics equipments are used for regulating the actuation, including the rate, force and 'R' wave triggering for co-coordinating with inherent cardiac activity when present.

The polymer used for producing the nanoparticles loaded magnetic membrane according to the present invention can be any suitable polymeric material depending upon the desired end use/application. For biomedical purposes the membrane is preferably a biocompatible polymeric material such as the Biospan segmented polyurethane (PU) with sufficient elastic property and can serve as a base for preparing the desired magnetic membrane. The nanoparticles-loaded magnetic membrane as of the present invention is substantially flexible to take any desired shape to cooperate as a support function.

The magnetic particles used for embedding in said polymeric material are selected from $Fe_3O_4$ nanoparticles, Cobalt nanoparticles, or any other superparamagnetic nanoparticles having extremely large magnetic moment and large susceptibility to magnetic fields and the sizes of nanoparticles are selected from a range between 1 nm to 100 nm and preferably 20-30 nm. The magnet assembly comprising the permanent magnets that are rare earth magnets such as NdFeB, SmCo and the like and an electromagnet.

Reference is now given for the accompanying FIG. 4 that schematically illustrate a system according to the present invention showing the disposition of all its essential elements including the displaceable magnetically actuating nanoparticles loaded polymeric membrane therein to artificially actuate as a blood pump means under the action of magnets of selectively controlled magnetic field strength. The figure shows the heart inside the human body, where the said device drains blood from the left ventricle of the heart by a cannula "a" and blood is pumped out of the device by a long cannula "c" into the aorta thereby doing the work of the heart which itself is failing and ineffective. The enlarged view of the device is shown below the first one in the figure and it is the invention. The blood is then pumped out as a result of the displacement of the magnetic nanoparticles loaded magnetic PU membrane (e) used in the device of this invention, actuated by one permanent magnets (h) and one electromagnet (j). The blood exits through an outflow limb (c) guarded by a valve (d) back into the aorta of the patient when the magnetic membrane is attracted by the action of a permanent magnet (h) of required field strength and the electromagnet remains inactivated. The electro magnet (j) is worn outside the body at close proximity to the body wall with no wires traversing the skin barrier (i) and deflects the magnetic membrane at the position (f) when electrically energized to desired field strength, overcoming the field of attraction of the permanent magnet (h) placed on the other side of the magnetic membrane (e).

It is clearly apparent from the magnetically actuated artificial PU pump according to tie invention can basically comprise of a polyurethane housing of the pump wherein the blood flows in into the housing through an inlet tube provided with one way valve that allows flow of blood inside but stops flow in reverse direction. Similarly, the blood flows out from said housing through a outlet tube and provided with one way valve means that allows flow of blood outside the housing/chamber after reaching a definite pressure by way of displacement pumping of the magnetic diaphragm and prohibit flow in reverse direction. It is further evident from the illustrative embodiment that the magnetic nanoparticles loaded polyurethane membrane is adapted to get displaced or provided with desired pulsating motion of desired strength and frequency under magnetic action in a system comprising an electromagnet located outside the body wall that displaces the magnetic membrane to position when energized with electrical pulse current of selective magnitude so as to overcome the force of attraction by the permanent magnet. However, in absence of the energization of the electromagnet, the magnetic membrane gets suitably deflected towards the permanent magnet. The repetition of energization and de-energization of the electromagnet thus enable providing the pulsating motion to the magnetic membrane with desired rate, force, frequency enough to enable functioning of the device as an independent/stand-alone total artificial heart pump to replace a failing heart.

Advantageously in said artificial heart pump, a function generator is provided for supplying periodic electric signal to the electromagnet so that the electromagnet simultaneously produces magnetic field and thus attracting and releasing the nanoparticles loaded magnetic PU membrane. In this process, the back and forth motion of the magnetic membrane can be utilized for the systolic and diastolic movement of the heart. The frequency of the input electric signal to the electromagnet can be synchronized with the desired heart beat. The electronics equipments are provided for regulating the actuation, including the rate, force and "R" wave triggering for coordinating with inherent cardiac activity when present. The above system thus provides for the required artificial biocompatible PU heart pump as magnetically activated cardiac assist device adapted for assisting impaired heart under the actuation of selective magnetic field capable of providing both systolic and diastolic movements. Importantly by means of the electronic control equipment it is possible to generate appropriate magnetic field strength such that the membrane moves back and forth enabling said artificial PU heart pump providing the basic motion and drive force of a displacement pump to assist in muscle activation for auricle/ventricle for blood pump/circulation or act as a Total Artificial Heart Pump.

The electromagnet is employed, by passing a dc input current supply, such that when there is no current through the electromagnet, the magnetic membrane remains attracted by the permanent magnet, located on the opposite side of the electromagnet. When the dc current is increased through the electromagnet, the membrane is pulled away from the permanent magnet and when the force due to the electromagnet overcomes that of the permanent magnet, the membrane is displaced towards the electromagnet. Again when the current through the electromagnet is reduced and made zero the permanent magnet is adapted to pull back the membrane. The desired to and fro displacement motions of the nanoparticles loaded membrane thus can be achieved with the arrangement shown in this figure.

Reference is now invited to the accompanying FIG. 5 that schematically-illustrates an alternative illustration of the magnetically actuating polymeric membrane based-displacement pump means for a different application directed to solve the problem associated with post myocardial infarction (heart attack) remodeling and dilated cardiomyopathy. It is known in the art that in case of heart failure due to heart attacks, one portion of the heart, typically the anterior wall, stops contracting initially due to abrupt cut off in its blood supply. Later, due to ventricular remodeling, this area dilates, becomes aneurysmal. In effect what this does is during systole, the blood from the heart, instead of being ejected into the aorta, lot of it is captured in the ventricle itself, as the aneurysmal segment expands out. This sets in motion a chain of events which results in severe heart failure. Also, clots tend to form in this region. Currently, in these patients, that region of the heart which expands and bulges out during systole, is either excised or excluded from the circulation by a prosthetic patch. This benefits the circulation, by preventing dyskinesia (outward bulging) thus making the circulation more efficient and by reducing the size of the ventricle. This procedure will work only if the rest of the heart contracts well. Also, any patch material which is used, will be non contractile. So, no new contracting muscle is added.

A biomaterial, polyurethane with magnetic nanoparticles embedded inside, which can be actuated by an external magnetic force has the potential of being a patch which can impart regional contractility to the heart and can be an ideal material with which to do these endo-ventricular patch repairs. The actuation of the patch needs to be synchronized with the hearts contractility so that the patch moves in synchrony with the rest of the heart.

In this proposed model of FIG. 5, the magnetic nanoparticles loaded magnetically displaceable polymeric membrane (6) is the magnetic patch inside the ventricular cavity (5), which moves back and forth due to an external magnetic force. The inflow cannula is left atrial blood entering the left ventricle. Out-flow cannula is the aorta (3). Inflow valve is the patients own mitral valve (2), which is usually normal, or leaking in which case, it can be repaired. The outflow valve, is the patients aortic valve (4). The magnetic patch is actuated by two magnets outside the body (9 and 10). Insertion of the patch is simple, either by open surgery or can be mounted on a circular stent and inserted percutaneously. The electromagnet with power supply for magnetization being placed outside the body wall, with no wire crossing the skin barrier and thereby, eliminating chances of developing possible infections.

Reference is now given to the accompanying FIG. 6(*a*) showing the anatomy of chest and abdominal portion, wherein the disposition of abdominal diaphragm having normal deflection, which facilitate the rhythmic respiration.

Reference is next given to the accompanying FIG. 6(*b*) that schematically illustrates the viscera of abdominal cavity and chest wherein the paralyzed right dome of the abdominal diaphragm is assisted by the nanoparticles loaded magnetic membrane disposed on the right dome of the diaphragm affected with phernic paralysis and actuated by an electromagnet placed outside body wall.

The diaphragm having a right dome (b', b") and a left dome (a), which is a muscle separating the chest and abdominal cavities is one of the most important muscles needed for normal breathing.

During inspiration, when we inhale air in, the diaphragm moves down towards the abdominal cavity (d), increasing the space in the thoracic cavity, causing a negative intrathoracic pressure causing the lungs (c) to expand, facilitating the movement of air into the lung.

In certain disease conditions the diaphragmatic muscle (a, b', b") can be paralysed, involving both the right and left sides or only one side. This can be congenital, or following injury to the phrenic nerve which is the nerve supplying the diaphragm. This can also happen following traumatic or other injuries to the spinal cord or in diseases like poliomyelitis, ascending polyneuritis etc where the nerves supplying the diaphragm are directly affected. Under these circumstances, especially if both the diaphragmatic muscles are paralysed, the person cannot breathe and needs to be on artificial ventilation. Phrenic nerve pacing can help if the phrenic nerve is intact from the neck downwards but not in case of spinal injuries. The outlook for these unfortunate patients is currently very poor, life-long artificial ventilation, the well known example being Christopher Reeves, who played superman in a movie.

In this situation, a magnetic nanoparticles embedded polyurethane membrane (f) as of the invention is sutured onto a paralysed diaphragm (b') e.g. right dome and activated by an electromagnet triggered to coincide with the initial respiratory effort, so that the diaphragm can move down like normal, making it possible for the patient to breathe normally.

Reference is next invited to accompanying FIGS. 7(*a*) to (*c*) that illustrate schematically how the magnetic nanoparticles loaded flexible membrane based magnetic actuation system can be utilized to solve very common complaint of dribbling of urine or fecal matter in elderly people due to the incompetence of normal sphincters FIG. 7(*a*). Artificial sphincters are available to solve the problem but are not very efficient. FIGS. 7(*b*) and 7(*c*) shows the application of electro-magnetically operated magnetic nanoparticles loaded polymeric flexible membrane based actuation system wherein the polymeric membrane replace the ineffective sphincters and are actuated selectively according to need by remote operation of an electromagnet selectively disposed to retain/to void the stored urine from the urinary bladder. Thus this membrane permits us to design more efficient sphincters.

It is thus possible by way of the present invention to develop a magnetic nanoparticles loaded membrane based displacement system for artificial heart support and other medical appliances. The artificial bio-compatible PU heart pump device involving magnetic nanoparticles loaded PU displaceable magnetic membrane would be adapted to function as a cardiac assist device by generating pulsating motion of said membrane to thereby act as an standalone total artificial heart device to replace a totally failing heart or assisting an impaired heart by supporting both the systolic and diastolic functions of the heart under the action of selectively disposed magnetic fields of desired strength and character. It is adapted to provide displacement motion of the flexible membrane based on requisite-controlled frequency, strength and amplitude in a simple, cost effective, reliable and bio-compatible manner. It facilitates mechanical/displacement work in a number of mechanically or any displacement specific actuated devices such as activation of paralyzed diaphragmatic muscles to aid in the breathing for patients with phrenic paralysis in quadriplegics. It can also be used to aid artificially emptying the urinal bladder in paralytic patients or possible use as artificial sphincters in safe, reliable and cost effective manner and thus capable of wide application in medical appliance industries and others.

We claim:

1. An artificial heart support system comprising:
    a support pumping system for blood circulation as in a human heart inside of a human body comprising:
    a housing having an inlet tube with a first one way valve for the flow of blood inside said housing from the heart and an outlet tube with a second one way valve for the flow of blood out of said housing into a blood vessel in the human body;
    a displaceable magnetically actuating nanoparticle loaded polyurethane membrane disposed within said housing wherein the membrane is flexible and has embedded therein superparamagnetic nanoparticles which have an extremely large magnetic moment and a large susceptibility to a magnetic field beyond that of paramagnetic particles and wherein the nanoparticles are in the size range of 1 nm to 100 nm;
    a permanent magnet having a magnetic field of attraction configured to be disposed inside the human body and in proximity to said housing such that the permanent magnet enables maintaining an usual attracted disposition of the membrane having embedded therein superparamagnetic nanoparticles with respect to said permanent magnet in the housing; and
    an electromagnet configured to be placed outside and in close proximity to a body wall of the human body and opposite to said permanent magnet in proximity to said housing configured for placement inside the human body;
    the membrane thus disposed within said housing and between said permanent magnet and said electromagnet on either side of said membrane, to generate a displaceable and pulsating magnetic motion of the membrane between said permanent magnet and said electromagnet;
    the membrane having embedded therein superparamagnetic nanoparticles actuated under said pulsating magnetic motion generated by said permanent magnet and said electromagnet under a selectively controlled magnetic field strength;
    said electromagnet having a DC input supply for being selectively energized for said selectively controlled magnetic field strength with a periodic electric signal such that when there is no current through the electromagnet, the membrane having embedded therein superparamagnetic nanoparticles remains attracted by the permanent magnet located on the opposite side of the electromagnet and on supply of DC current and said DC current's increase through the electromagnet, the membrane having embedded therein superparamagnetic nanoparticles is pulled away from the permanent magnet and displaced towards the electromagnet and again when the DC current through the electromagnet is reduced and made zero the permanent magnet is adapted to pull back the membrane having embedded therein superparamagnetic nanoparticles such that in the process a pumping action is generated to take in and drive out the blood from the housing adapted to facilitate the circulating motion of blood as in the human heart;
    a function generator for supplying said periodic electric signal to said electromagnet having the DC input supply to support the operation of the membrane having embedded therein superparamagnetic nanoparticles synchronized with the systolic and diastolic movements of the heart based on synchronization of frequency of a DC input supply signal to said electromagnet;
    said electromagnet configured to be placed outside and in close proximity to said body wall of the human body with DC input power supply based on said function generator operable from outside the human body free of any wire crossing a human body skin barrier providing for magnetic actuation of the membrane having embedded therein superparamagnetic nanoparticles so as to effect said displaceable and pulsating magnetic motion of the membrane in said housing when electrically energized under said periodic electrical signal to said field strength overcoming the magnetic field of attraction of said permanent magnet placed on the other side of the membrane.

2. The artificial heart support system as claimed in claim 1 wherein said outlet tube is configured to connect to said blood vessel in the human body for the flow of blood out of said housing into said blood vessel and comprises a longer cannula with respect to the inlet tube, the inlet tube comprising a cannula for the flow of blood inside said housing from the heart; said electromagnet is energized with a periodic input signal with a frequency synchronized with a heartbeat and involving said function generator regulating the rate, force and "R" wave triggering to coordinate with inherent cardiac activity.

* * * * *